United States Patent [19]

Imaki et al.

[11] Patent Number: 5,359,121
[45] Date of Patent: Oct. 25, 1994

[54] GLYCINE DERIVATIVE MONOSODIUM SALT TETRAHYDRATE

[75] Inventors: Katsuhiro Imaki; Hirohisa Wakatsuka, both of Osaka, Japan

[73] Assignee: Ono Pharmaceutical Co., Ltd., Osaka, Japan

[21] Appl. No.: 182,366

[22] Filed: Jan. 18, 1994

Related U.S. Application Data

[62] Division of Ser. No. 963,552, Oct. 20, 1992, abandoned.

[30] Foreign Application Priority Data

Oct. 25, 1991 [JP] Japan .................. 3-306925

[51] Int. Cl.$^5$ ........................... C07C 311/15
[52] U.S. Cl. ................................. 560/13
[58] Field of Search ........................ 560/13

[56] References Cited

U.S. PATENT DOCUMENTS 5,017,610  5/1991  Imaki .

FOREIGN PATENT DOCUMENTS 298650  1/1987  European Pat. Off. .
2184122  1/1987  United Kingdom .

OTHER PUBLICATIONS

Reiner Sustmann et al., Houben–Weyl, vol. E5, Georg Thieme Verlag, Stuttgart, 1985, pp. 496–504.
Hydration of Poly(ethylenimine); Chatani, Yozo Contemp. Top. Polym. Sci., 4, 531–543; 1984 Search report.

*Primary Examiner*—José G. Dees
*Assistant Examiner*—Samuel Barts
*Attorney, Agent, or Firm*—Stevens, Davis, Miller & Mosher

[57] ABSTRACT

N-[o-(p-pivaloyloxybenzenesulfonylamino)benzoyl]glycine monosodium salt tetrahydrate of the formula (I):

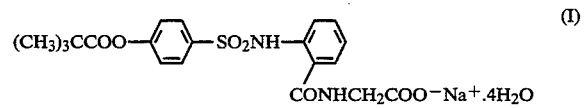

is non-hygroscopic, homogeneous and stable compound, and has an inhibitory effect on elastase. Accordingly, the compound may be useful for the treatment and/or prevention of diseases induced by the abnormal enhancing of degradation of elastin, collagen fiber and/or proteoglican by the action of elastase, e.g., pulmonary emphysema, atherosclerosis, rheumatoid arthritis, etc.

1 Claim, 1 Drawing Sheet

GLYCINE DERIVATIVE MONOSODIUM SALT TETRAHYDRATE

This application is a division of application Ser. No. 07/963,552, filed Oct. 20, 1992, now abandoned.

SUMMARY

This invention relates to a glycine derivative. More particularly, this invention relates to:
1) N-[o-(p-pivaloyloxybenzenesulfonylamino)benzoyl]glycine monosodium salt tetralydrate of the formuola (I):

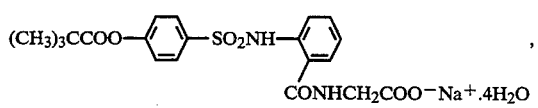

2) process for the preparation thereof,
3) pharmaceutical agents containing it as active ingredient, and process for the preparation of N-[o-(p-pivaloyloxybenzenesulfonylamino)benzoyl]glycine of the formula (II):

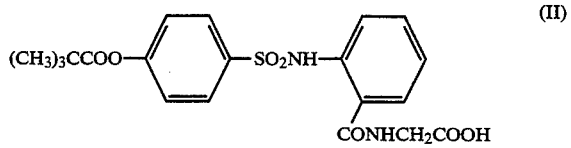

as an intermediate for preparing the compound of the formula (I).

BACKGROUND

Lysosomal hydrolases of neutrophils have an important role for an organisms defense reaction against tissue damage caused by microbe or inflammation, etc.

Elastase and cathepsin G, which belong to neutral serine proteinase locally existed in azurophil granule mainly play a part in decomposition of a connective tissue.

Especially, elastase degrades elastic connective tissue by cleaving the cross-liking of elastin which directly maintains the elasticity of lung tissue etc., and by cleaving hydrophobic part of protein [J. Cell. Biol., 40, 366 (1969)] and degrades the cross-linking area of collagen selectively as well as elastin [J. Biochem., 84, 559 (1978)], and it acts on tissue proteins such as proteoglycans etc. [J. Clin. Invest., 57, 615 (1976)]. Therefore, elastase plays an important role in the metabolism of connective tissue.

Elastase is inactivated by α1-proteinase inhibitor ($\alpha_1$-P1) that is a common inhibitor for serine, proteinase in vivo and the unbalance of enzyme and inhibitor system causes the destruction of the tissue [Schweiz. Med. Wshr., 114, 895 (1984)].

The turnover of elastin in normal tissue is very slow [Endocrinology, 120, 92 (1978)], but the pathological acceleration in degradation of elastin is found under various unsound states such as pulmonary emphysema [Am. Rev. Respir. Dis., 110, 254 (1974)], atherosclerosis [Lab. Invest., 22, 228 (1970)] and rheumatoid arthritis [in Neutral Proteases of Human Polymorphonuclear Leukocytes, Urban and Schwarzenberg, Baltimore—Munich (1978), page 390], suggesting the relationship of elastase and diseases [Infection Inflammation Immunity, 13, 13 (1983)].

RELATED ARTS AND ITS PROBLEMS

With the background as mentioned above, recent studies and developments on elastase inhibitors have been energetically conducted, and various substances inhibiting elastase have been proposed and many patent applications have been filed.

For example, in the specification of the European Patent Publication No. 347,168, it is described that the compounds of the formula (A):

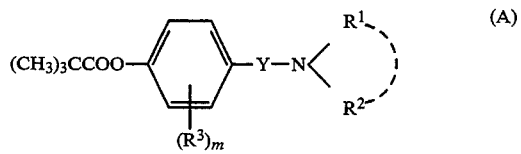

wherein Y represents sulfonyl group or carbonyl group,
(1) $R^1$ and $R^2$, which may be the same or different, each represent
(1) a hydrogen atom,
(2) an alkyl group of up to 16 carbon atom(s)
(3) a group of the formula:

wherein X represents single-bond, sulfonyl group, an alkylene group of up to 4 carbon atom(s) or an alkylene group of up to 4 carbon atom(s) substituted by a —COOH group or a benzyloxycarbonyl group,

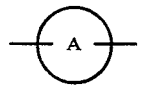

represents a carbocyclic ring or a heterocyclic ring, n represents an integer of 1 to 5, $R^4$ represents, the same or different,
(a) a hydrogen atom or an alkyl group of up to 8 carbon atom(s),
(b) an alkoxy group of up to 14 carbon atom(s),
(c) an alkylthio group of up to 6 carbon atom(s),
(d) a hydroxy group, a halogen atom, a nitro group or a trihalomethyl group,
(e) a group of the formula: —$NR^{41}R^{42}$ wherein $R^{41}$ and $R^{42}$ each represents, same or different, a hydrogen atom or an alkyl group of up to 4 carbon atom(s),
(f) a tetrazole group,
(g) a sulfonic acid group or a hydroxymethyl group,
(h) a group of the formula: —$SO_2NR^{41}R^{42}$ wherein $R^{41}$ and $R^{42}$ have the same meanings as described hereinbefore,
(i) a group of the formula: —$Z^{41}$—$COOR^{43}$ wherein $Z^{41}$ represents a single-bond, an alkylene group of up to 4 carbon atom(s) or an alkenylene group of from 2 to 4 carbon atoms, $R^{43}$ represents a hydrogen atom, an alkyl group of up to 4 carbon atom(s) or the benzyl group, (j) a group of the formula: —CONR$^{41}$R$^{42}$ wherein R$^{41}$ and R$^{42}$ have same meanings as described hereinbefore, (k) a group of the formula: —COO—Z$^{4-}$ 2—COOR$^{43}$ wherein Z$^{42}$ represents an alkylene group of up to 4 carbon atom(s), R$^{43}$ represents a hydrogen atom, an alkyl group of up to 4 carbon atom(s) or the benzyl group, (l) a group of the formula: —COO—Z$^{4-}$ 2—CONR$^{41}$R$^{42}$ wherein Z$^{42}$, R$^{41}$ and R$^{42}$ have same meanings as described hereinbefore, (m) a group of the formula: —OCO—R$^{45}$ wherein R$^{45}$ represents an alkyl group of up to 8 carbon atom(s) or the p-guanidinophenyl group, (n) a group of the formula: —CO—R$^{46}$ wherein R$^{46}$ represents an alkyl group of up to 4 carbon atom(s), (o) a group of the formula: —O—Z$^{43}$—COOR$^{450}$ wherein Z$^{43}$ represents an alkylene group of up to 6 carbon atom(s), R$^{450}$ represents a hydrogen atom, an alkyl group of up to 8 carbon atom(s) or p-guanidinophenyl group, (p) a group of the formula:

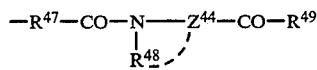

wherein >N—Z$^{44}$—CO represents an amino acid residue, R$^{47}$ represents a single-bond or an alkyl group of up to 4 carbon atom(s), R$^{48}$ represents a hydrogen atom or an alkyl group of up to 4 carbon atom(s), and R$^{49}$ represents the hydroxy group, an alkoxy group of up to 4 carbon atom(s), an amino group, an amino group substituted by one or two an alkyl group(s) of up to 4 carbon atom(s), a carbamoylmethoxy or a carbamoylmethoxy group substituted by one or two alkyl group(s) of up to 4 carbon atom(s) at the nitrogen atom of the carbamoyl group, or wherein

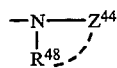

represents a heterocyclic ring containing 3 to 6 carbon atoms and R$^{47}$ and R$^{49}$ has each the same meaning as described hereinbefore, or (2) R$^1$, R$^2$ and nitrogen atom(s) bonded to R$^1$ and R$^2$ together represent a heterocyclic ring containing at least one nitrogen atom(s) and substituted by —COOH, or an unsubstituted heterocyclic ring containing at least one nitrogen atom(s), R$^3$ represents (1) a hydrogen atom,
(2) a hydroxy group,
(3) an alkyl group of up to 6 carbon atom(s),
(4) a halogen atom,
(5) an alkoxy group of up to 4 carbon atom(s) or
(6) an acyloxy group of 2 to 5 carbon atoms, m represents an integer of up to 4, and non-toxic salts and acid addition salts thereof, having an inhibitory effect on elastase, and therefore, are useful for the treatment of diseases induced by elastase, e.g., pulmonary emphysema, atheroscleorosis, rheumatoid arthritis etc.

The compound of the formula (11) corresponds to that of the said formula (A), wherein Y is a sulfonyl group, one of R$^1$ and R$^2$ is a hydrogen atom, and the other is a group of the formula:

in which X is a single bond,

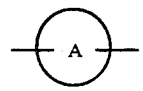

is carbocyclic ring (benzene ring), n is 1, and R$^4$ is a group of the formula:

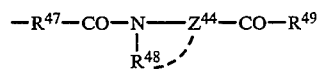

in which >N—Z$^{44}$—CO is an amino acid residue (glycine), R$^{47}$ is a single bond, R$^{48}$ is a hydrogen atom and R$^{49}$ is a hydroxy group, and is specifically disclosed in Example 2 (63) in the specification of the European Patent Publication No. 347,168 mentioned above.

The present inventors have prepared various non-toxic salts of the compound of the formula (II) in order to improve the solubility of that compound. As the result of the investigation, it has been found that a sodium salt thereof is the most suitable. However, it has turned out that the monosodium salt of the compound of the formula (II) is hygroscopic and it is hydrated with the laspe of time on exposure to air, finally to form the tetrahydrate via a mixture of monohydrate, dihydrate and trihydrate.

Such hygroscopic property is undesirable for the purpose of offering pharmaceuticals whose character in physical chemistry is always homogeneous and stable.

MEANS IN ORDER TO SOLVE THE PROBLEM

As the result of energetic investigations conducted in order to solve the above problem, the present inventors have synthesized from the beginning, the monosodium salt of the compound of the formula (II) as its tetrahydrate (i.e., that of the formula (I)) and have found that the tetrahydrate is excellent as a pharmaceutical formulation because of the absence of a hygroscopic property and the maintenance of a regular composition.

There is no description of its tetrahydrate itself and no suggestion thereof in the specification of the aforesaid European Patent Publication No. 347,168. Further, it is unexpected from the specification of the European Patent Publication No. 347,168, that the hygroscopic property of the monosodium salt of the compound of the formula (II) can disappear by forming the tetrahydrate thereof.

BRIEF DESCRIPTION OF THE DRAWING

The accompanying

DISCLOSURE OF THE INVENTION

Figure 1:
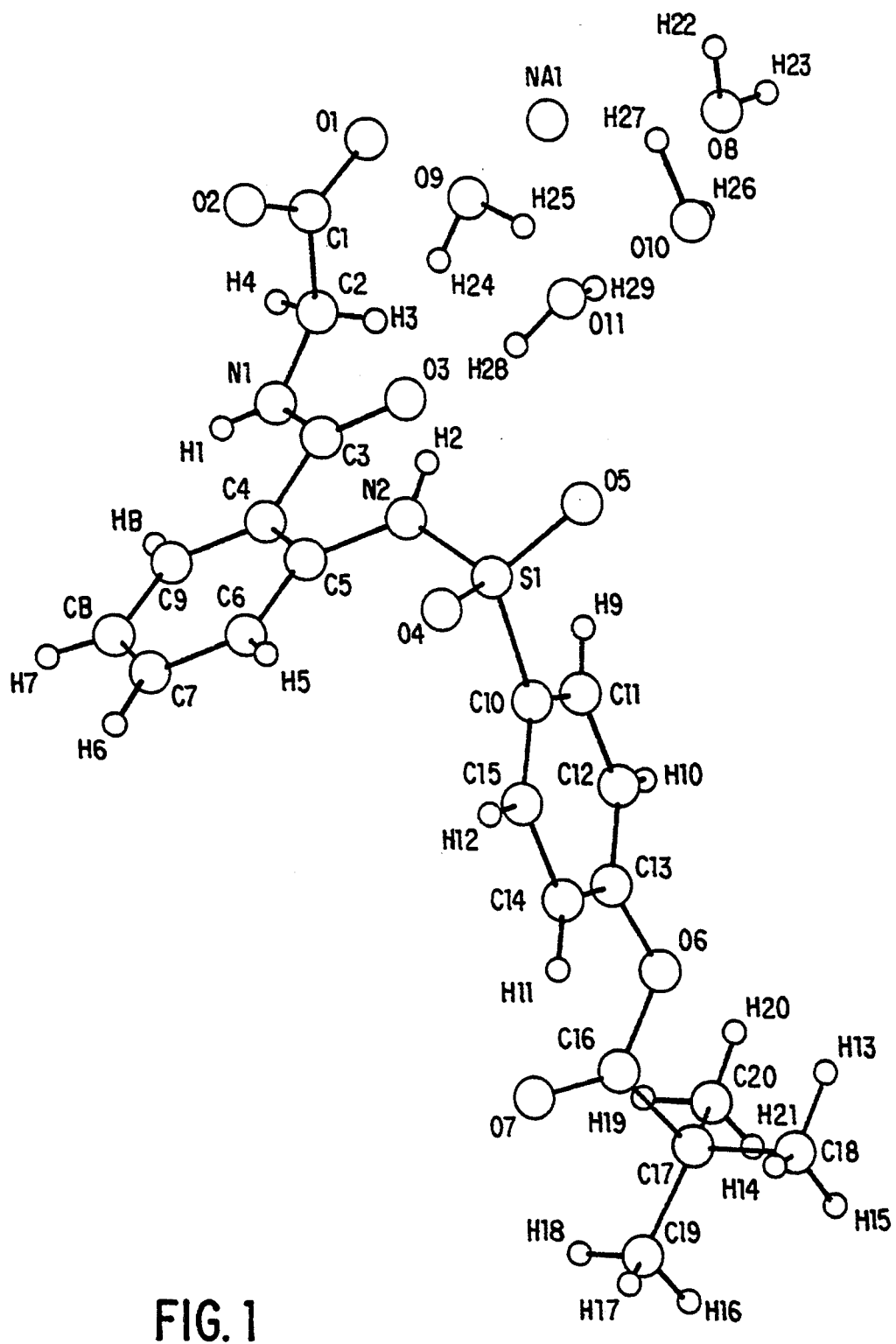
FIG. 1 shows a molecular structure based on X-ray diffraction of N-[o-(p-pivaloyloxybenzenesulfonylamino)benzoyl]glycine monosodium salt tetrahydrate as obtained in Example 3 below.

The present invention relates to
1) N-[o-(p-pivaloyloxybenzenesulfonylamino)benzoyl]glycine monosodium salt tetrahydrate of the formula (I):

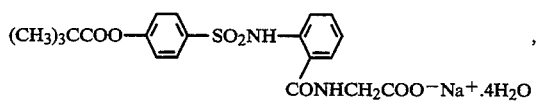

2) a process for the preparation thereof,
3) pharmaceutical agents containing it as active ingredient, and
4) a process for the preparation of N-[o-(p-pivaloyloxybenzenesulfonylamino)benzoyl]glycine of the formula (II):

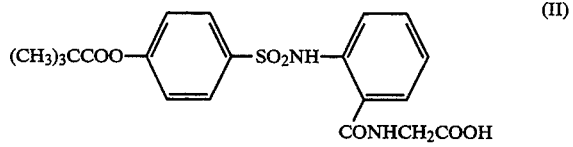

as an intermediate for the compound of the formula (I).

PROCESS FOR THE PREPARATION

The compound of the present invention of the formula (I) may be prepared by, for example, reacting the compound of the formula (II):

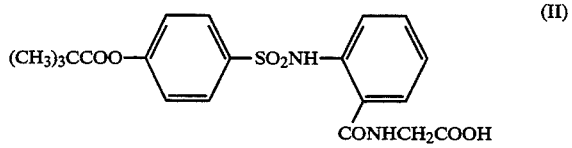

with an aqueous solution of 1.0 to 1.2 molecular equivalents of sodium hydroxide, sodium bicarbonate or sodium carbonate in an inert organic solvent (e.g., tetrahydrofuran (THF), dioxan, acetone etc.), recrystallizing the thus obtained crude crystals from water or a mixture of water miscible organic solvent and water (e.g., aqueous methanol, aqueous ethanol, aqueous propyl alcohol, aqueous acetone, aqueous dioxane etc.), and then air-drying the thus obtained crystals for more than 24 hours.

The present invention also provides a novel process for the preparation of the compound of the formula (II).

The specification of the European Patent Publication No. 347,168 shows that the compound of the formula (II) may be prepared according to a series of reactions depicted in the following scheme [A] (a part relating to the compound of the formula (II) is only extracted).

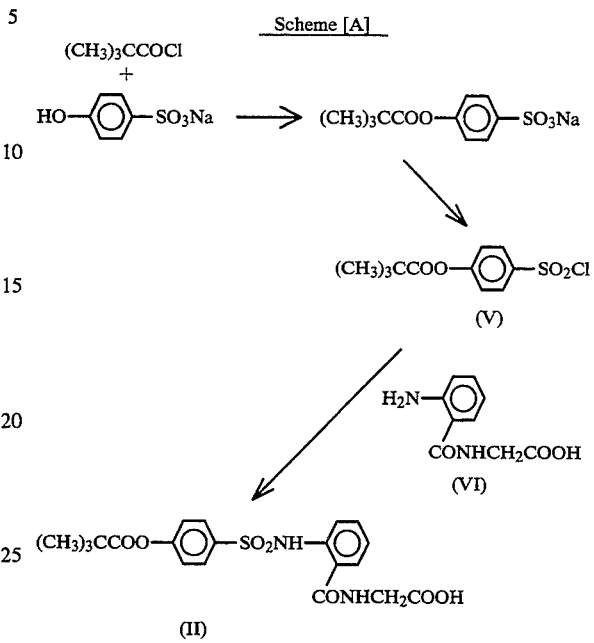

However, the following problem exists with the method for the preparation of the compound of the formula (II), as disclosed in the specification of the European Patent Publication No. 347,168, when that method is industrially carried out. That is, the compound of the formula (V) may react with not only an amino group but also partially with a carboxyl group in the formula (VI) in the amidation in scheme [A] because of fairly weak nucleophilicity of the amino group in the compound of the formula (VI). The mixed acid anhydrides may be prepared by this reaction and various by-products may be formed by the reaction. This fact makes it very difficult to improve the yield of the compound of the formula (II) (the yield of the compound of the formula (II) from that of the formula (V) is about 30%).

Accordingly, the method disclosed in the above specification is not necessarily satisfactory as the method for the industrial preparation of the compound of the formula (II).

Thereupon, as the result of further investigations into the process for the preparation of the compound of the formula (II), the present inventors have found that it can be industrially advantageously prepared by using a series of reactions depicted in the following scheme [B].

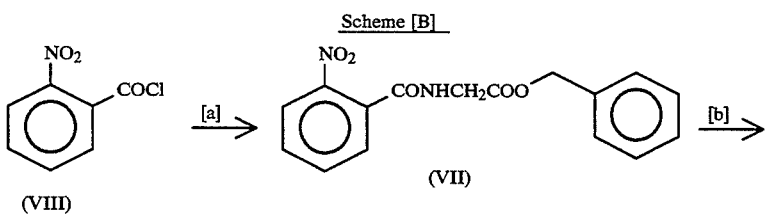

Scheme [B]

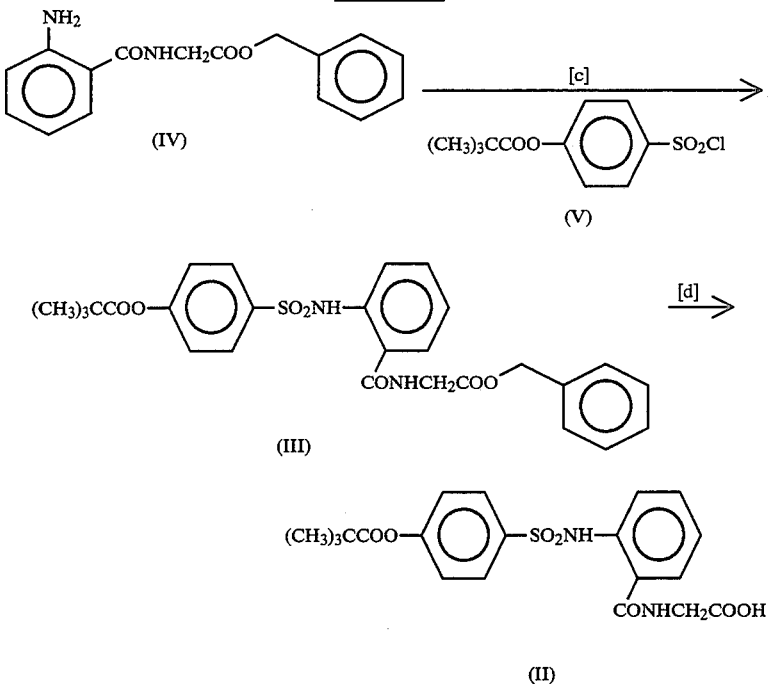

In scheme [B], the use of the compound of the formula (IV) in which the carboxyl group is protected by a benzyl group, in a sulfonamidation reaction (step [c]), decreases the formation of by-products, as compared with the conventional method in scheme [A] where the compound of the formula (VI) is used. Further, the compound of the formula (III) prepared by such a sulfonamidation reaction can be easily purified and can be quantitatively reduced to that of the formula (II) to obtain that compound in high purity and yield (the yield of the compound of the formula (II) from that of the formula (IV) is about 85%).

Each step in scheme [B] is explained in detail.

Step [a], which is the amidation, may be carried out by reacting an acyl halide with the amine of the formula (IX):

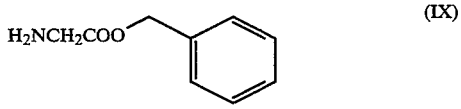

in the presence of an amine (e.g., triethylamine, pyridine, picoline, etc.), in an insert solvent [e.g., a halogenated hydrocarbon (methylene chloride, chloroform, carbon tetrachloride, tetrachloroethane, hexachloroethane, etc.), an ether (tetrahydrofuran (THF), tetrahydropyran, dioxan, diethyl ether, dimethyl ether, diisopropyl ether, dipheny ether, ethyl methyl ether, etc.) a benzene analogue (benzene, toluene, xylene, etc.)], at a temperature of $-20°$ C.$\sim 50°$ C.

Step [b], which is the reduction, may be carried out by reacting the nitro compound in the presence or absence of an inert solvent [e.g., an ether (the same meaning as described hereinbefore), an alcohol (methanol, ethanol, propanol, etc.), water or the mixture thereof], using iron, zinc, or tin and an acid (e.g., concentrated hydrochloric acid, concentrated sulfuric acid, acetic acid, etc.) at from room temperature to the reflux temperature of the solvent, or by reacting in the presence of an alcohol (the same meaning as described hereinbefore), using sodium borohydride ($NaBH_4$) and nickel chloride ($NiCl_2$), at a temperature of $-20°$ C.$\sim 50°$ C., or a system of sodium sulfide/ammonium chloride/aqueous solution of ammonia, by reacting using in the presence or absence of an inert solvent [e.g., an alcohol (the same meaning as described hereinbefore), an ether (the same meaning as described hereinbefore), or using a system of sodium hydrosulfite ($Na_2S_2O_4$)/aqueous solution of ammonia in the presence or absence of an inert solvent [e.g., an alcohol (the same meaning as describe hereinbefore), an ether (the same meaning as described hereinbefore)], or by reacting in a mixture of N,N-dimethylformamide (DMF) or 1,3-dimethyl-2-imidazolinone (DMI), and acetic acid, in the presence of raney nickel at normal or elevated pressure of hydrogen gas, at a temperature of 30° C.$\sim 100°$ C., preferably 35° C.$\sim 40°$ C.

Step [c], which is the sulfonamidation, may be carried out by reacting a sulfonyl chloride of the formula (V) with a compound of the formula (IV), in the presence of an amine (the same meaning as described hereinbefore) in an inert solvent [e,g., a halogenated hydrocarbon (the same meaning as described hereinbefore), an ether (the same meaning as described hereinbefore) or without a solvent, at a temperature of $-20°$ C.$\sim 50°$ C.

Setp [d], which is the reduction, may be carried out by reacting a compound of the formula (III) in an inert solvent [e.g., halogenated hydrocarbon (the same meaning as described hereinbefore), an ether (the same meaning as described hereinbefore), an alcohol (the same meaning as described hereinbefore), DMF, acetic acid, ethyl acetate, or the mixture of two or more of them] in the presence of a hydrogenation catalyst (e.g., palladium on carbon, palladium black, palladium, platinum dioxide, nickel, raney nickel, etc.) at normal or elevated pressure of hydrogen gas, at a temperature of 0° C.~200° C., preferably at room temperature.

The starting materials and reagents employed in the process for the compound of the preparation of the present invention are known per se, or may be prepared by known methods.

For example, the compound of the formula (VIII) is on the market, and the process for the preparation of the compound of the formula (V) is described in the specification of the European Patent Publication No. 347,168.

EFFECT OF THE INVENTION

N-[o-(p-pivaloyloxybenzenesulfonylamino)benzoyl]glycine monosodium salt tetrahydrate, of the formula (I) in the present invention, is a non-hygroscopic, homogeneous and stable compound, and has an inhibitory effect on elastase. Accordingly, the compound may be useful for the treatment and/or prevention of diseases induced by the abnormal enhancing of degradation of elastin, collagen fiber and/or proteoglican by the action of elastase, (e.g., pulmonary emphysema, atherosclerosis, rheumatoid arthritis, etc.) in mammals, especially in human beings.

Additionally, the process for the preparation of the compound of the formula (II), in the present invention, is industrially advantageous to obtain it in high purity because (i) the use of the benzyl ester of the formula (IV) in the step of sulfonamidation with that of the formula (V) decreases the formation of by-products and improves the yield, and (ii) the compound of the formula (III) can be easily purified and the reduction of the following step can be quantatively carried out.

The compound of the formula (II) obtained by the method of the present invention can be easily converted into its monosodium salt tetrahydrate of the present invention of the formula (I) by recrystallizing from an aqueous solvent.

The hygroscopicity and usueful pharmacological effect of the compound of the present invention have been confirmed by various experiments.

1. EXPERIMENT OF HYGROSCOPICITY (Method of Experiment)

N-[o-(p-pivaloyloxybenzenesulfonylamino)benzoyl]glycine monosodium salt tetrahydrate (the compound of the present invention) and N-[o-(p-pivaloyloxybenzenesulfonylamino)benzoyl]glycine monosodium salt (the comparison compound) were left at a temperature of 25° C., at humidity of 75%. The hygroscopicity of each compound was measured by the ratio of its weight to lapse of time. The result is shown in the following Table 1.

TABLE 1

| lapse of time (hr) | the present invention compound | the comparison compound |
| --- | --- | --- |
| 0 | 1.00 | 1.00 |
| 1 | 1.00 | 1.04 |
| 2 | 1.00 | 1.07 |
| 3 | 1.00 | 1.10 |
| 5 | 1.00 | 1.14 |
| 7.33 | 1.00 | 1.15 |
| 9.33 | 1.00 | 1.15 |
| 28 | 1.00 | 1.15 |

(Result)

It was recognized that the present compound had no change of its weight, though the comparison compound increased its weight with lapse of time. Accordingly, it can be said that the present compound is a non-hygroscopic, homogeneous and stable compound.

2. INHIBITORY EFFECT ON ELASTASE

The test was carried out by a slight modification of the method of Bieth et al [see Biochem. Med., 75, 350 (1974)] using elastase from human neutrophil. Namely, it is a spectrophotometric method using the synthesized substrate [succinyl-alanyl-prolyl-alanyl-p-nitroanilide (Suc-Ala-Pro-Ala-pNA, produced by the peptide laboratory)] which has comparatively high specificity on neutrophil elastase.

The reaction mixture consisted of 1 mM Suc-Ala-Pro-Ala-pNA (dissolved in N-methylpyrrolidone to the concentration of 100 mM, and then adding 1/100 amount of the solution to the reaction mixture.), 0.1M Tris-HCl buffer solution (pH 8.0), 0.2M sodium chloride aqueous solution, the sample solution of various concentrations and enzyme solution in a final volume of 1.0 ml was then incubated at 37° C. for 30 minutes. The reaction was stopped by the addition of 100 μl of 50% acetic acid into the reaction mixture, and then p-nitroanilide released was measure on absorbance of 405 nm with spectrophotometer. Inhibition percentage and $IC_{50}$ value, of the test compound were calculated.

The result showed that the $IC_{50}$ value of the compound of the present invention, of the formula (I), was 0.046.

TOXICITY

The toxicity of the compound of the present invention was very low, and therefore it may be said to be safe for pharmaceutical use.

APPLICATION FOR PHARMACEUTICALS

The present compound of the formula (I) has an inhibitory effect on elastase. Accordingly, it is useful for the treatment and/or prevention of diseases induced by the abnormal enhancing of the degradation of elastin, collagen fiber and/or proteoglican, by the action of elastase (e.g., pulmonary emhysema, atherosclerosis, rheumatoid arthritis, etc.).

For the purpose above described, the compounds of the formula (I) of the present invention may normally be administered systemically or partially, usually by oral or parenteral administration.

The doses to be administered are determined depending upon age, body weight, symptom, the desired therapeutic effect, the route of administration, and the duration of the treatment etc. In the human adult, the doses per person per dose are generally between 50 mg and 500 mg, by oral administration, up to several times per day, and between 10 mg and 200 mg, by parenteral administration up to several times per day, or by continuous administration between 1 and 24 hrs. per day from vein.

As mentioned above, the doses to be used depend upon various conditions. Therefore, there are cases in which doses lower than or greater than the ranges specified above may be used.

When administering of the compounds of the present invention, it is used as solid compositions, liquid compositions, or other compositions for oral administration, as injections, liniments or suppositories etc. for parenteral administration.

Solid compositions for oral administration include compressed tablets, pills, capsules, dispersible powders, and granules.

Capsules include hard capsules and soft capsules.

In such compositions, one or more of the active compound(s) is or are admixed with at least one inert diluent (lactose, mannitol, glucose, hydroxypropyl cellulose, microcrystalline cellulose, starch, polyvinylpyrrolidone, magnesium metasilicate aluminate, etc.). The compositions may also comprise, as is normal practice, additional substances other than inert diluents: e.g. lubricating agents (magnesium stearate, etc.), disintegrating agents (cellulose calcium glycolate, etc.), stabilizing agents (lactose, etc.), and assisting agents for dissolving (glutamic acid, asparaginic acid, etc.).

The tablets or pills may, if desired, be coated with a film of gastric or enteric material (sugar, gelatin, hydroxypropyl cellulose or hydroxypropylmethyl cellulose phthalate, etc.), or be coated with more than two films. And further, it may be include capsules of absorbable materials such as gelatin.

Liquid compositions for oral administration include pharmaceutically-acceptable solutions, emulsions, suspensions, syrups and elixirs.

In such compositions, one or more of the active compound(s) is or are contained in inert diluent(s) commonly used in the art (purified water, ethanol, etc.).

Besides inert diluents, such compositions may also comprise adjuvants (wetting agents, suspending agents, etc.), sweetening agents, flavoring agents, perfuming agents, and preserving agents.

Other compositions for oral administration include spray compositions which may be prepared by known methods and which comprise one or more of the active compound(s).

Spray compositions may comprise additional substances other than inert diluents: e.g. stabilizing agents (sodium sulfite etc.), isotonic buffer (sodium chloride, sodium citrate, citric acid, etc.).

For preparation of such spray compositions, for example, the method described in the U.S. Pat. No. 2,868,691 or 3,095,355 may be used.

Injections for parenteral administration include sterile aqueous or non-aqueous solutions, suspensions and emulsions. In such compositions, one more of active compound(s) is or are admixed with at least one of inert aqueous diluent(s) (distilled water for injection, physiological salt solution, etc.) or inert non-aqueous diluent(s) (propylene glycol, polyethylene glycol, olive oil, ethanol, POLYSOLBATE80 (registered trade mark), etc.).

Injections may comprise additional ingredients other than inert diluents: e.g. preserving agents, wetting agents, emulsifying agents, dispersing agents, stabilizing agents (lactose, etc.), tonicity agents, buffering agents, assisting agents such as assisting agents for dissolving (glutamic acid, asparaginic acid, etc.).

They may be sterilized for example, by filtration through a bacteria-retaining filter, by incorporation of sterilizing agents in the compositions or by irradiation. They may also be manufactured in the form of sterile solid compositions, for example, by freeze-drying, and which may be dissolved in sterile water or some other sterile diluent(s) for injection immediately before used.

Other compositions for parenteral administration include liquids for external use, and endermic liniments (ointment, etc.), suppositories and pessaries which comprise one or more of the active compound(s) and may be prepared by per se know methods.

REFERENCE EXAMPLES AND EXAMPLES

The following reference examples and examples illustrate the present invention, but do not limit the present invention.

The solvents in the parentheses show the developing or eluting solvents and the ratios of the solvents used are by volume in thin layer chromatographic (TLC) separation. Unless otherwise specified, infrared absorption spectrum (IR) was measured by the KBr method.

Reference Example 1

N-(2-nitrobenzoyl)glycine benzyl ester

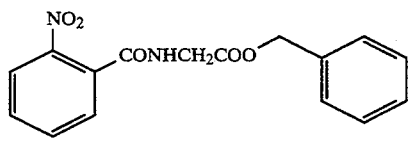

Triethylamine (4.6 ml) was added to a mixture of glycine benzyl ester p-toluene sulfonic acid salt (4.049 g) and methylene chloride (20 ml). To the mixture thus obtained, 2-nitrobenzoyl chloride (1.322 ml) was added dropwise under cooling with ice, and the mixture was stirred for one hour at room temperature.

The reaction solution was acidified by adding 1N hydrochloric acid, and the organic layer was washed with water, an aqueous solution of sodium bicarbonate, water, and a saturated aqueous solution of sodium chloride, successively, dried over magnesium sulfate and concentrated under reduced pressure to give the title compound (3.16 g) having the following physical data.

TLC: Rf 0.7 (chloroform: methanol: acetic acid=30:3:1).

Reference Example 2

N-(2-aminobenzoyl)glycine benzyl ester

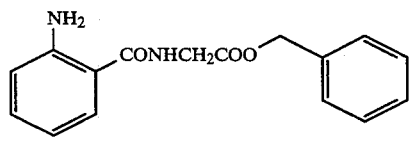

Powder of iron (3.02 g) was added by portions to a solution of the nitro compound (2.82 g) obtained in Reference Example 1 in a mixture of THF (18 ml) and water (9 ml) at room temperature.

2N hydrochloric acid (1.08 ml) was added dropwise to the mixture, and the mixture was stirred overnight at room temperature. 2N aqueous solution of sodium hydroxide (1.2 ml) was added to the obtained reaction solution, and the mixture was filtered through celite and extracted with ethyl acetate. The extract was washed with water and a saturated aqueous solution of sodium chloride, successively, dried over magnesium sulfate and concentrated under reduced pressure to give the title compound (2.05 g) having the following physical data.

TLC: Rf 0.6 (chloroform: methanol: acetic acid=100:5:1).

Reference Example 3

N-(2-aminobenzoyl)glycine benzyl ester (another process for the preperation)

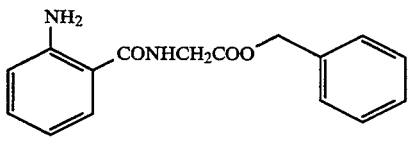

Raney nickel (8.4 g) was added by portions to 5N aqueous solution of sodium hydroxide (40 ml) at 50° C. over 30 minutes.

After the mixture was stirred for one hour at 50° C., raney nickel was washed with water. Then the water was displaced by 1,3-dimethyl-2-imidazolinone (DMI).

The mixture of raney nickel (4.2 g), the nitro compound (14 g) obtained in Reference Example 1, acetic acid (1.4 ml) and DMI (70 ml) was stirred for three hours at 40° C. under 25 atmospheric pressure of hydrogen in an autoclave.

The reaction solution was filtered through celite and the filtrate was poured into water. The resulting precipitate was collected by filtration. The solid was air-dried at room temperature for a week to give the title compound (11.2 g) having the following physical data.

TLC: Rf 0.6 (chloroform: methanol: acetic acid =100:5:1).

Example 1

N-[o-(p-pivaloyloxybenzenesulfonylamino)benzoyl]glycine benzyl ester

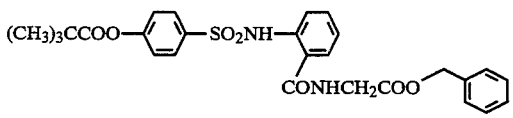

p-pivaloyloxybenzenesulfonyl chloride (prepared by the methods described in Reference Example 5 in the specification of the European Patent Publication No. 347,168; 2.66 g) was added to a mixture of the amine compound (2.28 g) obtained in Reference Example 2 or 3 and pyridine (36 ml) under cooling with ice and the mixture was stirred overnight at room temperature.

The reaction solution was added to a mixture of concentrated sulfuric acid and water (52 ml/100 ml) and extracted with ethyl acetate. The extract was washed with water, an aqueous solution of sodium bicarbonate, water and a saturated aqueous solution of sodium chloride, successively, dried over magnesium sulfate and concentrated under reduced pressure.

The residue was crystallized from n-hexane, and the crystals were filtered and dried under reduced pressure to give the title compound (3.70 g) as a pale yellow powder having the following physical data.

TLC: Rf 0.64 (ethyl acetate:n-hexane=1:1);

IR (cm$^{-1}$): $\nu$ 3425, 2976, 1757, 1642, 1597, 1540, 1495, 1457, 1406;

NMR (CDCl$_3$) $\delta$ (ppm): 7.75~7.65 (3H, m) 7.50~7.30 (6H, m), 7.18~7.00 (3H, m), 6.41 (1H, brs), 5.21 (2H, s), 4.04 (2H, d), 1.30 (9H, s).

Example 2

N-[o-(p-pivaloyloxybenzenesulfonylamino)benzoyl]glycine

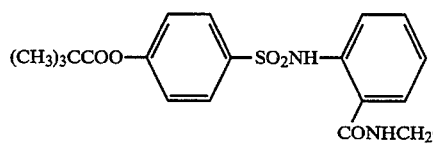

The mixture of the compound obtained in Example 1 (3.70 g), methanol (40 ml) and 10% palladium on carbon (390 mg) was stirred for three hours under an atmospheric pressure of hydrgen at room temperature.

The reaction solution was filtered through celite and concentrated under reduced pressure to give the title compound (2.91 g) as a white powder having the following physical data.

TLC: Rf 0.14 (chloroform: methanol: acetic acid =100:5:1);

IR (cm$^{-1}$): $\nu$ 3432, 2978, 1749, 1722, 1647, 1524, 1493, 1453, 1407;

NMR (CDCl$_3$+CD$_3$OD) $\delta$ (ppm): 7.77 (2H, d, J=8.5 Hz), 7.63 (1H, d J=7.5 Hz), 7.63 (1H, d, J=7.5 Hz), 7.46 (1H t, J=7.5 Hz), 7.15 (2H, d, J=8.5 Hz), 7.13 (1H, t, J=7.5 Hz). 3.98 (2H, s), 1.35 (9H, s).

Example 3

N-[o-(p-pivaloyloxybenenesulfonylamino)benzoyl]glycine monosodium salt tetrahydrate

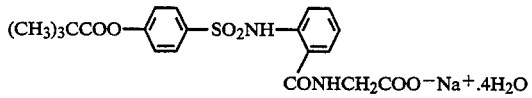

The compound obtained in Example 2 (8.69 g) was dissolved with heating into THF (40 ml). 5N aqueous solution of sodium hydroxide (4.2 ml) was added to the solution under cooling, and the solvent was distilled off under reduced pressure.

The obtained crude crystals were dissolved with heating into water (30 ml) and left at 5°~10° C. overnight. The precipitated crystals were collected by filtration, washed with ice-water and air-dried for 24 hours at room temperature to give the title compound (8.55 g) as a white powder having the following physical data.

| | Elemental analysis: | |
|---|---|---|
| | Calcd. (%) | Found (%) |
| C | 45.45 | 45.72 |
| H | 5.52 | 5.70 |
| N | 5.30 | 5.33 |

Moisture content (Karl Fischer's method): 13.65% (calcd. 13.63%)

IR (cm$^{-1}$): $\nu$ 3440, 2979, 1755, 1626, 1589, 1494, 1401, 1344, 1273, 1217, 1155, 1126, 1094, 942, 848, 754, 687. 600, 576;

Molecular structure: see the accompanying FIG. 1

Formulation Example

| N-[o-(p-pivaloyloxybenzenesulfonylamino) benzoyl] glycine monosodium salt tetrahydrate | 10 mg |
|---|---|
| distilled water | 500 ml |
| sodium chloride | 7 g |
| sodium carbonate (anhydride) | 1.5 g |
What is claimed is:
1. N-[o-(p-pivaloyloxybenzenesulfonylamino)benzoyl]glycine benzyl ester of the formula (III):
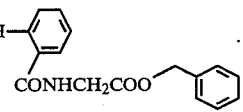

The following components were admixed in conventional manner. The solution was sterilized in conventional manner, placed in 5 ml portions into vials and freeze-dried to obtain 100 vials each containing 100 mg of the active ingredient.